(12) United States Patent
Brennan et al.

(10) Patent No.: US 6,450,975 B1
(45) Date of Patent: Sep. 17, 2002

(54) ULTRASONIC TRANSMISSION GUIDE WIRE

(75) Inventors: Lawrence Brennan; Douglas Gesswein, both of Temecula; Wayne Cornish, FallBrook; Robert J. Siegel, Venice, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,521

(22) Filed: Dec. 30, 1999

(51) Int. Cl.$^7$ .................................................. A61B 5/00
(52) U.S. Cl. ........................................................ 600/585
(58) Field of Search ................................ 600/585, 434; 606/159, 169; 604/20, 22

(56) References Cited

U.S. PATENT DOCUMENTS

| | | | |
|---|---|---|---|
| 4,721,117 A | 1/1988 | Mar et al. ................... 128/772 |
| 4,870,953 A | 10/1989 | DonMicheal et al. ......... 128/24 |
| 4,920,954 A | 5/1990 | Alliger et al. ................ 128/24 |
| 4,925,445 A | * 5/1990 | Sakamoto et al. .......... 600/585 |
| 5,163,421 A | 11/1992 | Bernstein et al. .......... 128/24.1 |
| 5,267,954 A | 12/1993 | Nita ............................ 604/22 |
| 5,304,115 A | 4/1994 | Pflueger et al. ............... 604/22 |
| 5,312,328 A | * 5/1994 | Nita et al. ................... 606/169 |
| 5,365,943 A | * 11/1994 | Jansen ........................ 600/585 |
| 5,368,557 A | 11/1994 | Nita et al. .................... 604/22 |
| 5,380,274 A | 1/1995 | Nita ............................ 604/22 |
| 5,382,228 A | * 1/1995 | Nita et al. ................... 606/169 |
| 5,397,293 A | 3/1995 | Alliger et al. ................. 601/2 |
| 5,411,476 A | 5/1995 | Abrams et al. ................ 604/95 |
| 5,417,672 A | 5/1995 | NIta et al. ................... 604/283 |
| 5,427,118 A | * 6/1995 | Nita et al. ................... 600/585 |
| 5,606,979 A | * 3/1997 | Hodgson ..................... 600/585 |
| 5,735,811 A | 4/1998 | Brisken ....................... 604/22 |
| 5,827,201 A | * 10/1998 | Samson et al. ............. 600/585 |
| 5,846,218 A | 12/1998 | Brisken et al. ............... 604/22 |
| 5,989,208 A | 11/1999 | Nita ............................ 604/22 |
| 6,007,514 A | 12/1999 | Nita ............................ 604/22 |
| 6,290,656 B1 | 9/2001 | Boyle et al. ................ 600/585 |
| 6,296,620 B1 | 10/2001 | Gesswein et al. ............ 604/22 |

* cited by examiner

Primary Examiner—Kevin T. Truong
(74) Attorney, Agent, or Firm—Fulwider Patton Lee & Utecht, LLP (57) ABSTRACT

The ultrasonic angioplasty transmission guide wire has regions of reduced cross-sectional diameter to improve flexibility and to compensate for degradation of longitudinal displacement due to acoustic losses along the length of the guide wire. The guide wire has a core of ultrasonic transmission material and an outer jacket surrounding a usable portion of the elongated shaft. The outer jacket is formed of a shrink tubing. At the proximal end are disposed threads configured to connect to a connecting device for an ultrasound transducer. The distal end comprises a smooth ball tip for atraumatic application of ultrasound energy to biological tissue. In one embodiment, the guide wire is formed of stainless steel. In another, the guide wire is formed at least partially of a superelastic metal alloy and in one case is formed at least partially of a shape memory alloy that exhibits superelastic properties when in its martensitic state. In one preferred embodiment, the guide wire is formed of a nickel-titanium alloy.

28 Claims, 5 Drawing Sheets

ULTRASONIC TRANSMISSION GUIDE WIRE

BACKGROUND

This invention relates generally to medical devices, and more particularly concerns an improved guide wire configured to conduct ultrasound energy for use in the ultrasonic treatment of lesions located in hollow anatomical structures.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having a balloon on the distal end thereof are introduced through the guiding catheter with the guide wire slidably disposed within an inner lumen of the dilatation catheter. The guide wire is first advanced into the patient's coronary vasculature until the distal end thereof crosses the lesion to be dilated and then the dilatation catheter is advanced over the previously introduced guide wire until the dilatation balloon is properly positioned across the lesion. The balloon may then be inflated to treat the lesion. Thereafter, a stent device may be located at the treated lesion, if deemed necessary.

In "ultrasonic" angioplasty, an ultrasonic angioplasty catheter is similarly advanced over a guide wire to an area of a vascular lesion or blockage, and mechanical vibration at ultrasonic frequencies, generated typically by a piezoceramic transducer located at the proximal end of the angioplasty catheter, is delivered along an ultrasonic angioplasty transmission member or wire to a distal catheter tip. When the distal catheter tip abuts the lesion, vibration of the distal end of the ultrasonic angioplasty transmission member removes the obstruction by mechanical impact and cavitation. The guide wire that is advanced so as to cross the lesion is useful in properly aligning the catheter and assisting in its progress through the lesion as the ultrasonically-vibrating distal tip ablates the lesion.

Advancement of a guide wire to a desired location within a passageway or vessel may be difficult or impossible in cases where there exists a total or near-total blockage of the passageway or vessel. For example, in percutaneous transluminal coronary angioplasty (PTCA) procedures, the presence of a complete occlusion within the lumen of a diseased coronary artery may prevent the tip of a guide wire from being advanced through such occlusion lesion. An angioplasty catheter may likewise be prevented from being advanced to a proper operative location across the occlusive lesion. In such instances, the inability to advance the guide wire through the fully occluded coronary vessel may necessitate abandonment of the PTCA procedure and/or the election of an alternative, more invasive, procedure such as cardio-thoracic surgery. Thus, it would be highly desirable to develop a guide wire that is capable of safely boring or creating a tunnel or passageway through a total or near-total occlusion.

In ultrasonic angioplasty techniques, accurate positioning of the ultrasound transmission member in the vasculature system to be treated requires that the guide wire first be properly located across the lesion. Should the lesion be a complete blockage or a blockage so complete that the guide wire cannot be positioned across the lesion, a highly flexible ultrasonic delivery system with a low profile, especially for coronary ultrasonic angioplasty procedures, so that the catheter can more easily navigate the various vascular passages to be advanced to the occlusion is desirable. Nickel-titanium superelastic alloys have been useful in these respects as an ultrasound transmission member. Tapering or narrowing the distal end of an ultrasound transmission member to enhance flexibility of the ultrasound transmission member at its distal end is known from U.S. Pat. No. 5,304,115 (Pflueger et al.). While such tapering or narrowing typically decreases the rigidity and improves the bendability of the ultrasound transmission member, a significant increase in amplitude of the ultrasonic energy occurs at the tapered or narrowed region. Such an increase in amplitude can cause an increased likelihood of fracturing or breakage of the ultrasound transmission member at that point during use. It would be desirable to provide a guide wire having increased flexibility and amplification of ultrasonic energy, yet still be less prone to fracturing or breakage.

Hence those skilled in the art have recognized a need for an improved guide wire capable of transmitting ultrasound energy and providing improved characteristics of strength, fatigue resistance, and elasticity for an ultrasonic delivery system for use in the treatment of intravascular blockages. In particular, a need has been recognized for an improved guide wire capable of transmitting ultrasonic energy from an ultrasound generating device located outside the body to a site within the body for purposes of ablating obstructive matter. The present invention fulfills these needs and others.

SUMMARY OF THE INVENTION

Briefly, and in general terms, the present invention is directed to an improved ultrasound transmission guide wire for use in biological passageways. In one more detailed aspect, the invention is directed to an improved guide wire for use in an ultrasonic angioplasty PTCA catheter system for ablating lesions in the vascular system of a patient.

Turning now to more detailed aspects, the invention is directed to an ultrasound transmission guide wire for use in an ultrasonic angioplasty device, the ultrasound transmission guide wire having an elongated shaft, a proximal end configured to be connected to an ultrasound transducer, and a distal end for applying ultrasonic energy to an area of vascular lesion, the ultrasound transmission guide wire comprising a distal portion with at least one amplification region of reduced cross-sectional diameter, a core of ultrasonic transmission material, and an outer jacket surrounding a usable portion of the elongated shaft. In a further aspect, the ultrasound transmission guide wire comprises threads disposed at its proximal end, the threads configured to connect to a connecting device for an ultrasound transducer to thereby communicate ultrasonic energy to the elongated shaft and to the distal end of the ultrasound transmission guide wire.

In yet further more detailed aspects, the ultrasound transmission guide wire comprises a first generally cylindrical section having a first cross-sectional diameter, and a second generally cylindrical section distal to the first section and having a second cross-sectional diameter that is smaller than the first cross-sectional diameter, the amplification region being formed at a proximal portion of the second generally cylindrical section. The ultrasound transmission guide wire further comprises a plurality of generally cylindrical sections, each of the plurality of generally cylindrical sections having reduced cross-sectional diameter relative to a proximal adjacent section resulting in a plurality of amplification regions in the cylindrical sections of reduced cross-sectional diameter. The ultrasound transmission guide wire further comprises a conically tapered section interposed between the first and second cylindrical sections. In further detail, the ultrasound transmission guide wire further comprises a plurality of conically tapered sections interposed between adjacent ones of the plurality of generally cylindrical sections.

Turning to other detailed aspects, the ultrasound transmission guide wire further comprises an enlarged application portion located at the distal end of the elongated shaft, the enlarged application portion configured to apply ultrasonic energy to a biological lesion. In more detail, the enlarged application portion comprises a rounded portion having a diameter exceeding the diameter of the elongated shaft immediately proximal to the rounded portion. And yet further, the enlarged application portion comprises a smooth ball tip having a diameter exceeding the diameter of the elongated shaft immediately proximal to the ball tip.

In another detailed aspect, the outer jacket is formed of a non-metallic material. Further, the outer jacket is formed of shrink tubing. In another aspect, the outer jacket is formed of rubber, and in yet a further aspect, the outer jacket is formed of plastic.

In regard to the material of the guide wire, in one aspect, the ultrasound transmission guide wire is formed at least partially of a superelastic metal alloy. In further aspects, the ultrasound transmission guide wire is formed at least partially of a shape memory alloy that exhibits superelastic properties when in its martensitic state, and further, the ultrasound transmission guide wire is formed of a nickel-titanium alloy.

In further features, an ultrasound transmission guide wire for use in an ultrasonic angioplasty device is provided, the ultrasound transmission guide wire having an elongated shaft, a proximal end configured to be connected to an ultrasound transducer, and a distal end for applying ultrasonic energy to an area of vascular lesion, the ultrasound transmission guide wire comprising a core including, in atomic percent, from about 28 to about 52 percent nickel, from about 48 to about 52 percent titanium, and up to about 20 percent of at least one alloying element selected from the group consisting of palladium, chromium, and hafnium. In more detailed aspects, the alloying element is hafnium or palladium, and is present, in atomic percent, in a range from about 3 to about 20 percent.

In another more detailed aspect, the alloying element is present, in atomic percent, in a range from about 5 to about 11 percent.

In another aspect, the alloying element is palladium. In yet another aspect, the alloying element is chromium and is present, in atomic percent, in a range up to about 3 percent. In more detail, the alloying element is present, in atomic percent, in a range from about 0.1 to about 1.0 percent, and in yet more detail, the alloying element is present, in atomic percent, in a range from about 0.2 to about 0.5 percent.

In another aspect, the ultrasound transmission guide wire comprises threads disposed at its proximal end, the threads configured to connect to a connecting device for an ultrasound transducer to thereby communicate ultrasonic energy to the elongated shaft and to the distal end of the ultrasound transmission guide wire.

These and other aspects and advantages of the invention will become apparent from the following detailed description and the accompanying drawings, which illustrate by way of example, the features of the invention.

DETAILED DESCRIPTION OF THE PREFERRED EMBODIMENTS

Figure 1:
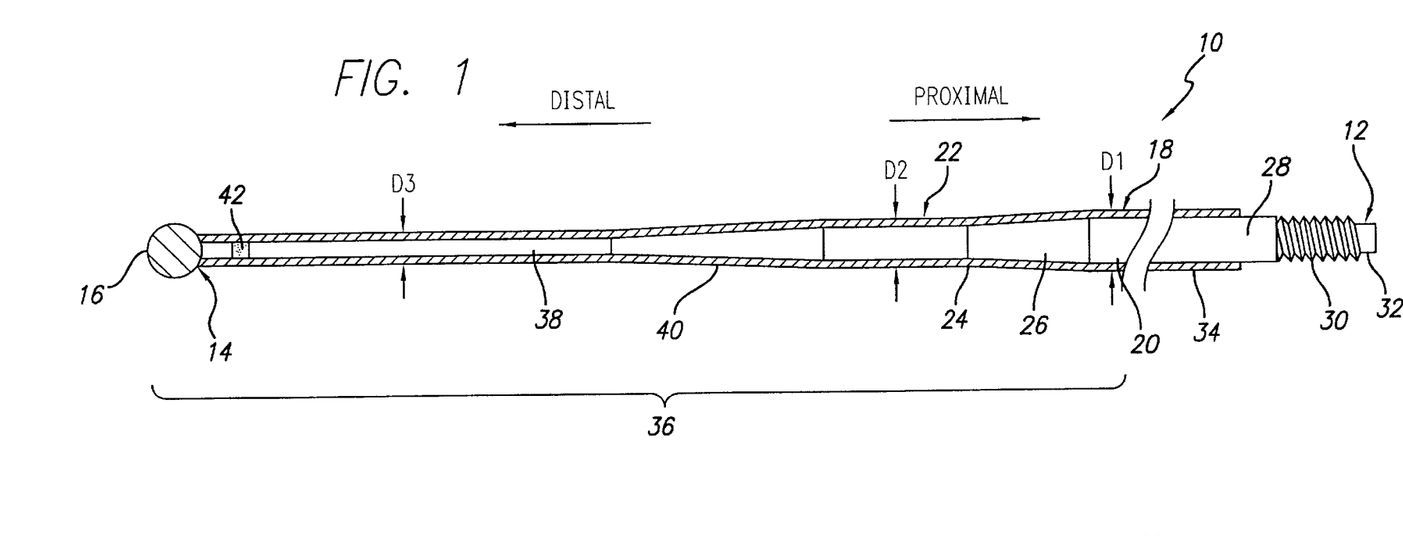
FIG. 1 is a side, partial cross-sectional view of an embodiment of an ultrasound transmission guide wire having a plurality of amplifier sections, threads on the proximal end, and an atraumatic ball at the distal end according to the principles of the invention.

Referring now to the drawings in more detail in which like reference numerals refer to like or corresponding elements among the views, there is shown in FIG. 1 an elongate ultrasound transmission guide wire 10 that has a proximal end 12 for connection with an ultrasound transducer (not shown) and a distal end 14 with a distal head 16, in this case an enlarged head, for applying ultrasonic energy to an area of vascular blockage. In a currently preferred embodiment, improved flexibility of the ultrasound transmission guide wire 10 is achieved by reducing the cross-sectional diameter of the ultrasound transmission guide wire at the distal end. Degradation of longitudinal displacement of the ultrasound transmission guide wire due to acoustic losses along its length between its proximal end 12 and its distal end 14 is compensated for by step amplifications. The ultrasound transmission guide wire is stepped to a lower diameter along one or more sections of the guide wire 10, as is illustrated in FIG. 1.

The ultrasound transmission guide wire 10 thus comprises a distal portion 18 having a first generally cylindrical section 20 with a first cross-sectional diameter D1, and a second generally cylindrical section 22 distal to the first section and having a second cross-sectional diameter D2 that is smaller than the first cross-sectional diameter D1. The second generally cylindrical section 22 has an amplification region 24 of reduced cross-sectional diameter, typically at a proximal end of the second generally cylindrical section 22 where transverse vibration of ultrasonic energy transmitted from the first generally cylindrical section is amplified. A conically tapered section 26 is preferably interposed between adjacent cylindrical sections of different diameters to provide a smooth transition area from one cylindrical section to the next. Each transition area preferably provides a smooth shift between adjacent cylindrical sections of different diameters to reduce stress concentrations due to transverse vibrations of the ultrasound transmission guide wire.

The ultrasound transmission guide wire 10 of FIG. 1 comprises an elongated shaft or core 28 having threads 30 formed on its proximal end 12. The most proximal portion has a bevel 32 to assist in locating the threaded portion 30 in an ultrasound transducer or connector (not shown). Disposed over a usable portion of the core 28 is an outer jacket 34.

In one presently preferred embodiment, the ultrasound transmission guide wire is formed of stainless steel. In another embodiment, the ultrasound transmission guide wire is formed of a heat treated superelastic alloy, such as that disclosed in U.S. Pat. No. 5,411,476 to Abrams et al. This nickel-titanium alloy, which is available from Fort Wayne Metals, in Fort Wayne, Ind., exhibits a superelastic property in the higher temperature range, demonstrates improved strength and elasticity prior to permanent deformation, and also good acoustic properties.

The superelastic alloy consists essentially of about 40 to 49% titanium, with a balance of nickel and up to 10% of one or more additional alloying elements that can be selected from the group of up to 3% each of iron, cobalt or chromium, and up to about 10% copper and vanadium, all by atomic percent. The alloy material is preferably cold worked, preferably by drawing, to effect a size reduction of about 30% to about 70% in the transverse cross section thereof. The cold worked material can then be given a memory-imparting heat treatment at a temperature of about 350° C. to about 600° C. for about 0.5 to about 60 minutes, while maintaining longitudinal stress on the elongated portion equal to about 5% to about 50%, preferably about 10% to about 30%, of the yield stress of the material, as measured at room temperature. Another method involves mechanically straightening the wire after the cold work, and then heat treating the wire at temperatures between about 300° C. and 450° C., preferably about 330° C. to about 400° C. For more consistent final properties, it is preferred to fully anneal the stock prior to cold working so that the material will always have the same metallurgical structure at the start of cold working and will have adequate ductility for subsequent cold working. Cold working of the metal other than drawing, such as rolling or swaging, can also be employed. Another nickel-titanium alloy that may also be suitable in forming the ultrasound transmission guide wire contains 50.8 atomic percent nickel, and is sold under the trade name TINEL by Raychem Corporation.

While the flexibility of the ultrasound transmission guide wire is improved by step reductions in diameter and the degradation of the ultrasonic power due to acoustic losses presented by the length of the wire is compensated for by step amplifications at the step reductions to a smaller diameter, increased stress concentration at these regions results. These stress concentrations are preferably reduced by placing the outer jacket 34 over the usable portion of the ultrasound transmission guide wire. As is illustrated in the diagram of FIG. 1, in one presently preferred embodiment, the outer jacket 34 is disposed completely around the core 28 of the ultrasound transmission guide wire along the usable portion to reduce transverse vibration, to thereby lower stress and lower the possibility of ultrasonic guide wire fractures of the ultrasound transmission guide wire, while allowing longitudinal movement of the ultrasound transmission guide wire. As shown in FIG. 1, the outer jacket 34 is tightly disposed around the core 28 from a position just distal to the threads 30 to a point just proximal to the enlarged distal ball 16, and can be made of shrink tubing, plastic or rubber, for example, although other similar materials that can reduce transverse vibration at the amplification regions of the ultrasound transmission guide wire may also be suitable.

Extending the outer jacket 34 to a position adjacent the threads 30 at the proximal end 12 of the core 28 locates it at the connection of the ultrasonic transducer to the ultrasound transmission guide wire (not shown), which represents one of the regions where the greatest amplification occurs due to a stepped reduction in diameter.

As should be readily apparent, additional generally cylindrical sections can be provided in sequence in the ultrasound transmission guide wire 10 that are of reduced cross-sectional diameter relative to a proximal adjacent section. As is illustrated in FIG. 1, the ultrasound transmission guide wire includes multiple segments or generally cylindrical sections at its distal end, with a conically tapered transition area located between adjacent segments. In FIG. 1, the ultrasound transmission guide wire 10 has a distal end 14 with a distal head 16 for applying ultrasonic energy to an area of vascular blockage. The ultrasound transmission guide wire 10 comprises a distal portion 36 having a first generally cylindrical section 20 with a first cross-sectional diameter D1, a second generally cylindrical section 22 distal to the first section and having a second cross-sectional diameter D2 that is smaller than the first cross-sectional diameter. The second generally cylindrical section 22 has an amplification region 24 of reduced cross-sectional diameter, typically at a proximal end of the second generally cylindrical section 22 where transverse vibration of ultrasonic energy transmitted from the first generally cylindrical section 22 is amplified. A conically tapered section 26 is preferably interposed between the first and second cylindrical sections. In the embodiment illustrated in FIG. 1, the distal portion 36 of the ultrasound transmission guide wire comprises a third generally cylindrical section 38 with a third cross-sectional diameter D3, which is smaller than the second and first cross-sectional diameters D2 and D1. Another conically tapered section 40 is located between the second and third generally cylindrical sections 22 and 38 to provide a smooth transition.

Also located at the distal portion 36 of the guide wire 10 is a radio opaque marker 42 for use in locating the distal tip during in vivo procedures. The marker may consist of any suitable material that shows up clearly under fluoroscope or other viewing technique. Although only one marker is shown, more may be used. Additionally, as can be seen, the marker is embedded in the core 28 and is therefore also covered by the outer jacket 34. This configuration will result in less stress and trauma to the patient.

Figure 2:
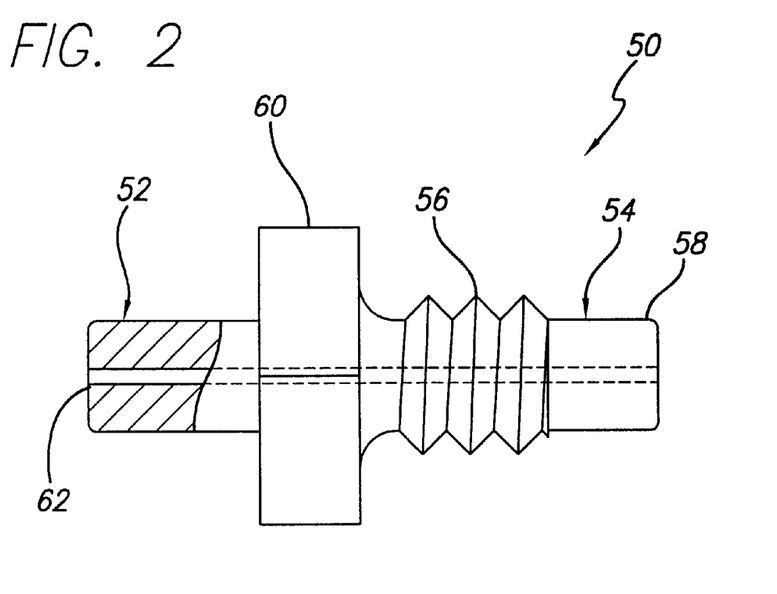
FIG. 2 is a side, partial cross-sectional view of a crimp screw for use in connecting the ultrasound transmission guide wire of FIG. 1 to an ultrasound transducer.
Figure 3:
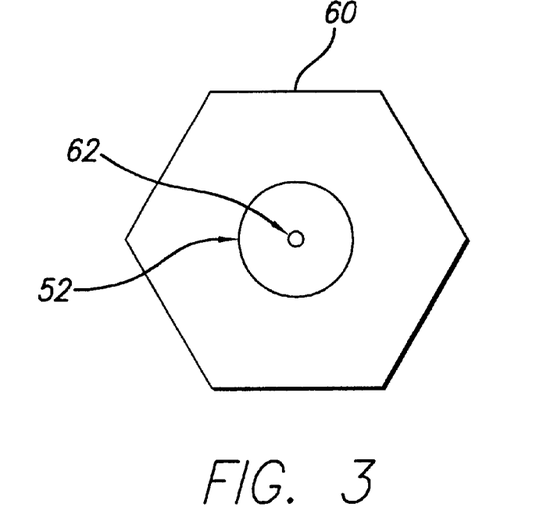
FIG. 3 is an end view of the crimp screw of FIGS. 2 showing the hexagonal outer configuration for use in rotating the screw with a tool, and showing the aperture for receiving the ultrasonic transmission guide wire for crimping.

Turning now to FIGS. 2 and 3, an alternate connection technique of the ultrasound transmission guide wire 10 to an ultrasound transducer is shown. In this embodiment, an intermediary device is used to provide more mechanical leverage for mounting the guide wire to the ultrasound transducer. A crimp screw 50 is shown that is used as a connector to an ultrasound transducer (not shown). The crimp screw 50 includes a distal portion 52 to receive the proximal end 12 of the guide wire 10 (FIG. 1) and a proximal portion 54 that is threaded 56 for connection to an ultrasound transducer. The proximal tip includes a bevel 58 to assist in locating the threaded portion 54 in an ultrasound transducer or connector. Located between the distal and proximal portions 52 and 54, is a mounting control section 60 that includes a hexagonal outer configuration for use in rotating the screw with a tool, thus providing increased mechanical leverage. An aperture 62 is formed in the distal portion 52 for receiving the proximal end of the guide wire. Although not shown, a crimp nut having a hole for receiving the guide wire is screwed into the aperture 62. Once the guide wire has been inserted in the aperture such that it extends to the proximal portion 54, the crimp screw may be rotated into position in the distal portion 52 of the crimp screw 50. The crimp nut may also contain a dampening material on its hole through which the guide wire passes to further steady the guide wire while it is undergoing ultrasonic vibration. Then, the proximal portion 58 may be crimped with a crimping tool to permanently fasten the guide wire in place. The crimp tool typically forms flat surfaces on the proximal portion 58. The crimp screw 50 may then be rotated into position in a transducer with an open-ended wrench or similar tool.

Turning to exemplary dimensions, the outer diameter of the core 28 of the guide wire may be 0.33 mm and with the outer jacket, the overall outer diameter of the guide wire may be 0.36 mm at the largest cylindrical section 20. The overall length of the crimp screw 50 may be 12.2 mm while the wall-to-wall diameter across the hexagonal section 60 may be 6.35 mm. The length of the hexagonal section was 2.16 mm in one embodiment. The length of the distal portion was 3.68 mm in one embodiment and the length of the proximal portion was 6.36 mm. The bevel formed at the distal tip was approximately 0.08 mm while the radius between the hexagonal section and the threads was 0.76 mm. The distance between the end of the threads and the proximal tip was 2.41 mm. The aperture 62 is the distal portion 52 was 0.33 mm with a tolerance of +0.03 mm and −0.00. The diameter of the distal section was 2.41 mm. The threads used were 6-32 UNC -2A. Other dimensions may be equally usable depending on the size of the guide wire and the dimensions of the ultrasound transducer. Such dimension changes are within the skill of one skilled in the art and no further comment is provided here.

Figure 4:
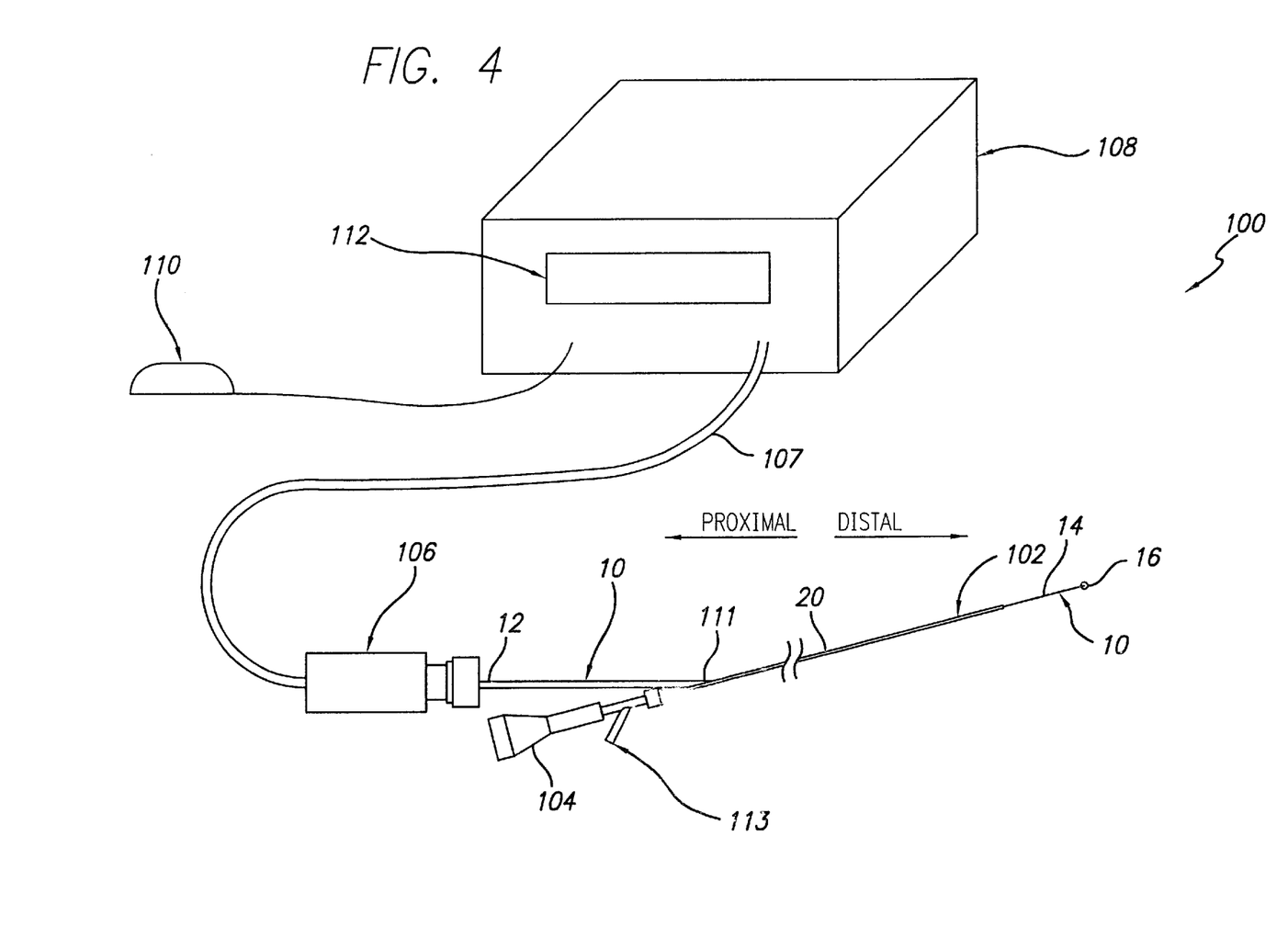
FIG. 4 is a general view of an angioplasty system incorporating an over-the-wire ultrasonic energy delivery catheter having an ultrasound transmission guide wire as shown in previous figures, the guide wire being introduced to the catheter through a side port at the proximal end.

The perspective view in FIG. 4 is of an over-the-wire ultrasound catheter system 100 in which a catheter 102 has a proximal end connector assembly 104 mounted on the proximal end thereof. As used herein, the term "over-the-wire" ("OTW") shall refer to a catheter that has a guide wire passage lumen formed within the body and extending from the proximal end to the distal end of the catheter such that a flexible guide wire may be advanced through the body of the catheter and out of a guide wire passage aperture formed in the distal end of the catheter. Returning to FIG. 4, an ultrasound transducer 106 is connected to the proximal end 12 of the guide wire 10. An ultrasound generator 108 having a foot-actuated on/off switch 110 is operatively connected to the ultrasound transducer 106 through an electrical cable 107 so as to send ultrasonic energy through the guide wire 10 when desired. The generator 108 includes a display 112 that presents certain information about the ultrasonic energy application process.

The distal end of the catheter 102 may include a dilatation balloon, a stent, or other apparatus depending on the configuration selected and is configured to be percutaneously inserted into a body vascular system and through tortuous body lumina to a desired location within the body vascular system. The proximal end of the catheter 102 includes a side arm 113. More side arms may be used such that cooling fluid or aspiration may be applied as needed. Such use of side arms is well known to those skilled in the art and no further description is provided herein.

In this embodiment, the ultrasound guide wire 10 is inserted into the catheter through a guide wire opening which is an elongated notch 111 in FIG. 4 and is formed at the proximal end of the catheter body 102. The notch 111 is configured to facilitate the insertion of a guide wire into a lumen of the catheter body 102 and the retraction of a guide wire from the lumen. Because of its size and location, the exchange of guide wires in the catheter body is facilitated. The ultrasound transmission guide wire 10 is received by the notch 111, extends through the catheter 102 in the OTW configuration discussed above, and exits the distal end of the catheter as shown.

Figure 5:
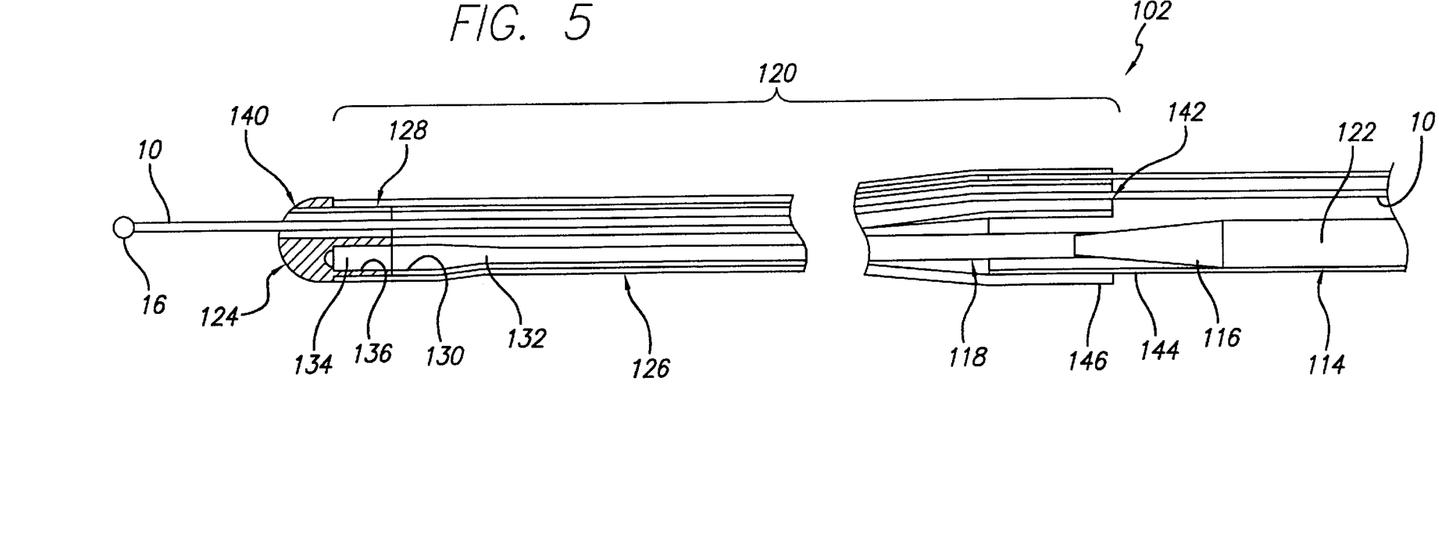
FIG. 5 is a sectional view of the distal end of the over-the-wire catheter of FIGS. 4 showing a distal head configured to apply ultrasound energy to a blockage and having the ultrasound transmission guide wire of FIG. 1 located in a guide wire aperture in the distal head of the catheter.

Turning now to FIG. 5, a sectional view of part of the catheter 102 of FIG. 4 is shown. An ultrasound transmission member 114 includes tapering 116 for amplification at its distal end. The taper 116 terminates in a reduced diameter section 118 of the ultrasound transmission member 114. Because the reduced diameter distal portion 118 of the ultrasound transmission member 114 is of smaller cross-sectional diameter and less mass, it is more flexible and less rigid than the proximal portion thereof. In the embodiment of the catheter 102 shown in FIG. 5, the outer diameter of the distal portion 120 of the catheter is also reduced to coincide with the reduced diameter distal portion 116, 118 of the ultrasonic transmission member 114, and also will exhibit less rigidity and greater flexibility than the remainder of the catheter body.

The present embodiment further includes an optional improvement to the ultrasound transmission member 114, said improvement comprising the disposition of a low friction coating or jacket 122 on the outer surface of all or a portion of the ultrasound transmission member 114. The low friction coating or jacket 122 may be disposed on the outer surface of the ultrasound transmission member so as to completely cover the ultrasound transmission member along its entire length, or along a discrete region or regions thereof. Such coating or jacket 122 may comprise a layer of low friction polymer material such as polytetrafluoroethylene (ptfe) (Teflon™ Dupont, Inc., Wilmington, Del.) or other plastic materials such as polyethylene. The coating or jacket 122 may be applied as a liquid and subsequently allowed to cure or harden on the surface of the ultrasound transmission member 114. Alternatively, the coating or jacket 122 may be in the form of an elongate tube slidably disposable over the outer surface of the ultrasound transmission member. Such coating or jacket 122 serves to prevent or diminish friction between the outer surface of the ultrasound transmission member 114 and the adjacent structures of the catheter or proximal end connector assembly 104 through which the ultrasound transmission member 114 extends.

A distal head 124 is firmly bonded, attached, or connected to the catheter body 126 such that the distal head is prevented from undergoing longitudinal or transverse movement separate from or relative to the catheter body. Additionally, such affixation of the distal head to the catheter body increases the conveyance of ultrasound energy into the distal portion of the catheter body 126, thereby resulting in enhanced cavitation effects created by the distal portion of the catheter body. Such bonding connection or attachment of the distal head 124 to the catheter body 126 may be accomplished by any suitable means. One means of attaching the distal head 124 to the catheter body 126 is through the use of an adhesive.

In the embodiment shown in FIG. 5, the adhesive is applied to the neck portion 128 of the distal head 124 prior to insertion thereof into the distal end of the lumen 130 of the catheter body 126. The adhesive may comprise any suitable adhesive, such as cyanoacrylate (e.g. Loctite™, Loctite Corp., Ontario, CANADA or Dron Alpha™, Borden, Inc., Columbus, OH) or polyurethane (e.g. Dymax™, Dymax Engineering Adhesive, Torrington, CN) to firmly bond and attach the distal head 124 to the catheter body 126.

The distal head 124 may be formed of any suitable rigid material such as metal or plastic. In devices wherein the distal head is formed of plastic, the surrounding plastic catheter body 126 may be thoroughly welded, heat sealed, or solvent welded to the plastic distal head 124, in accordance with the types of plastics employed.

In the alternative to the use of adhesives, various mechanical or frictional connectors, such as screw threads, lugs or other surface modifications formed on the neck portion 128 of the distal head 124, may be utilized to hold the distal head 124 in a fixed position relative to the catheter body 126. In such embodiments, corresponding grooves, detents or surface modifications may also be formed in the surrounding inner wall of the catheter body 126 so as to cooperate with any such threads, lugs or other surface modifications formed on the opposing surface of the distal head 124. Such threads, lugs or other surface modifications will be configured and constructed so as to mechanically or frictionally hold the distal head 124 in fixed position relative to the catheter body 126.

The distal head 124 is preferably formed of radio dense material so as to be easily discernable by radiographic means. Accordingly, the distal head 124 may preferably be formed of metal or, alternatively, may be formed of plastic, ceramic or rubber materials, optionally having one or more radio dense markers fixed thereto or formed therein. For example, the distal head 124 may be molded of plastic such as acrylonitrile-butadiene-styrene (ABS) and one or more metallic foil strips or other radio opaque markers may be affixed to such plastic distal head 124 in order to impart sufficient radio density to permit the distal head to be readily located by radiographic means. Additionally, in embodiments wherein the distal head is formed of molded plastic or other non-metallic material, a quantity of radio dense filler such as powdered bismuth or $BaSO_4$ may be disposed within the plastic or other non-metallic material of which the distal head is formed so as to impart enhanced radio density to the distal head.

Another feature to the catheter 102 is shown in FIG. 5. At the distal end 120, two tubular members are joined to result in the catheter shaft. In particular, a first tubular member 144 is used for the proximal and center sections of the catheter shaft while a second tubular member 146 is used for the distal section 120. As shown, the second, distal, tubular member 146 overlaps the first tubular member. The two members may be held together with adhesive. Such configuration to the catheter enables more cost effective manufacturing techniques as well as greater accuracy in manufacturing the catheter.

The ultrasound transmission member 114 is tapered outward 132 at its most distal extreme 134 to a size that fits within a cavity 136 formed in the distal head 124. Although this outward taper attenuates the ultrasonic energy somewhat, it results in greater stability of the ultrasound transmission member 114 at the distal end because there is more surface area provided for adhesive attachment to the distal head and less likelihood of breakage at the attachment point.

Also shown in FIG. 5 is the ultrasound transmission guide wire 10 disposed in a guide wire aperture 140 formed in the distal head 124. The catheter body may include a separate guide wire lumen 142 within which the guide wire is disposed. The guide wire may be introduced and retracted from the catheter body through the notch 111s shown in FIG. 4. Although the ultrasound transmission guide wire 10 shown in FIG. 5 includes the atraumatic smooth ball tip 16, the sections of step amplification and taper have been omitted for the purpose of clarity of illustration.

Figure 6:
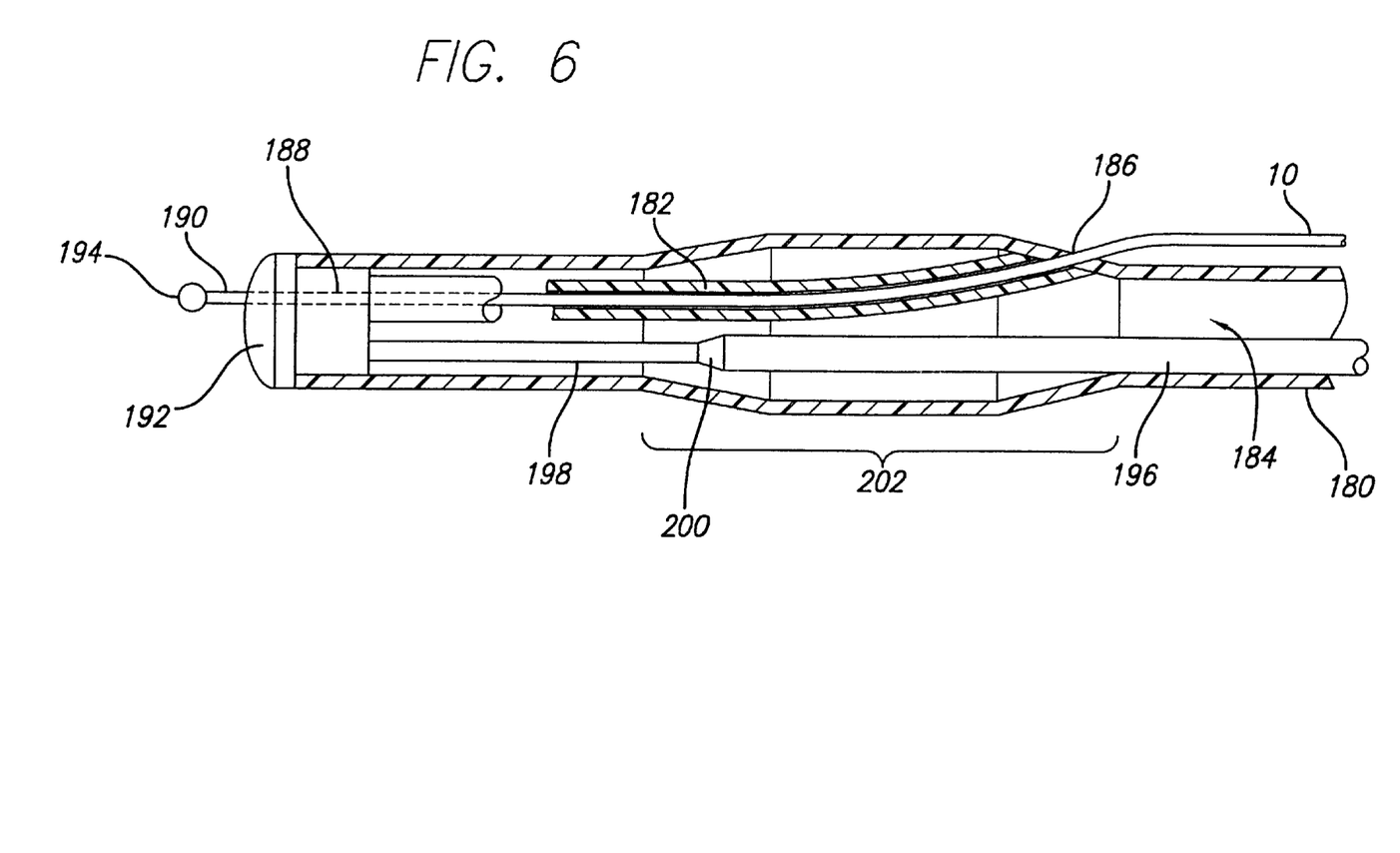
FIG. 6 is a diagram of a rapid exchange catheter using the ultrasound transmission guide wire of FIG. 1, and showing various details of the ultrasound catheter distal end.

Turning now to FIG. 6, a rapid exchange or "RX" embodiment of a catheter is shown. In this embodiment, the catheter body 180 may be provided with a distal guide wire passage tube 182 positioned within the inner bore or lumen 184 of the catheter body 180 and extending from a guide wire re-entry aperture 186 to the guide wire passage aperture 188 formed in the distal head 124 of the device. As such, the proximal end member of a guide wire 190 may be inserted into the distal head 192 of the catheter body 180 through the guide wire passage aperture 188 and subsequently disposed in a proximal direction through a guide wire lumen of the guide wire tube 182 to a point where the proximal end of the guide wire 190 emerges from the guide wire entry/re-entry aperture 186. After emerging from the guide were entry/re-entry aperture 186, the proximal portion of the guide wire 190 may extend and/or reside adjacent the outer surface of the proximal portion of the catheter body 180. The catheter body 180 and the guide wire 190 may then be distally and/or proximally repositioned, relative to one another, during the procedure. Also, if desired, the guide wire 190 may be fully withdrawn and extracted by pulling the guide wire in a proximal direction such that the distal tip 194 of the guide wire is pulled out of the guide wire entry/reentry aperture 186 and the guide wire 190 is subsequently fully withdrawn from the body 180, leaving only the ultrasound catheter in place in the patient.

The distal portion of the catheter shown in FIG. 6 contains many of the same elements shown in other figures. In particular, the distal head 192 is fixedly attached to the catheter body 180 through adhesive or other means. An ultrasonic transmission wire 196 is attached to the distal head 192 and has a stepped down length 198 with a conical transition area 200. An enlarged area 202 of the distal portion is used to accommodate the additional guide wire tube 182 in this RX embodiment.

Although embodiments shown and described herein include an OTW and an RX, other embodiments are possible that include combinations or hybrids of OTW and RX. As is apparent, a rapid exchange catheter system is easily used with the ultrasound transmission guide wire described and shown.

Figure 7:
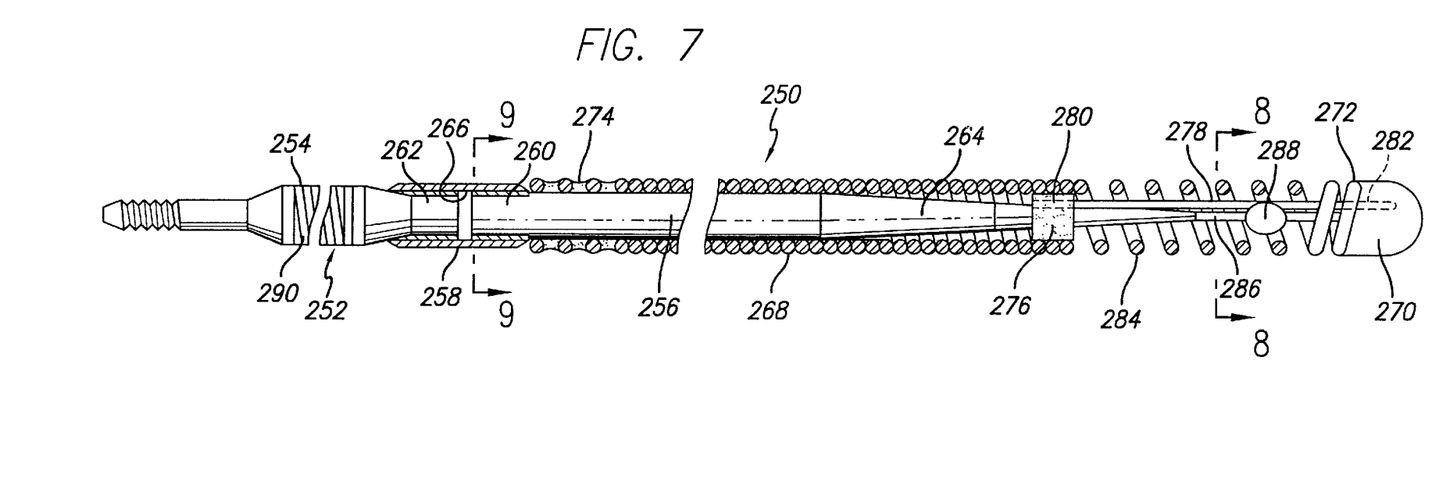
FIG. 7 is an elevational view of a guide wire embodying features of other aspects of the invention.
Figure 8:
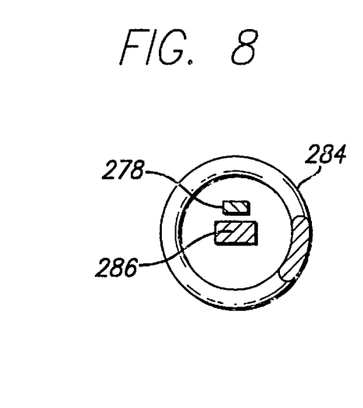
FIG. 8 is a transverse cross-sectional view of the guide wire of FIG. 7 taken along lines 8—8.
Figure 9:
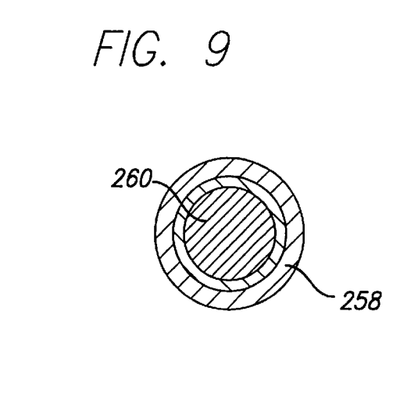
FIG. 9 is a transverse cross-sectional view of the guide wire of FIG. 7 taken along lines 9—9.

FIGS. 7, 8, and 9 illustrate an ultrasonic transmission guide wire 250 embodying features of the invention that is adapted to be inserted into a patient's body lumen, such as an artery. The ultrasonic guide wire 250 comprises an elongated core 252 comprising a relatively high strength proximal portion 254, a relatively short distal portion 256 that is formed substantially of superelastic alloy material, and a connector element 258 that is formed substantially of superelastic alloy material and that connects a proximal end 260 of the distal portion 256 to a distal end 262 of the proximal portion 254 into a torque transmitting relationship. The distal portion 256 has at least one tapered section 264 that becomes smaller in the distal direction. The connector element 258 is a hollow tubular shaped element having an inner lumen 266 extending therein that is adapted to receive the proximal end 260 of the distal portion 256 and the distal end 262 of the proximal portion 254. The ends 260 and 262 may be press fit into the connector element 258 or they may be secured therein by crimping or swaging the connector or by means such as a suitable adhesive or by welding, brazing, or soldering. The tubular connector 258 formed of superelastic alloy material provides a smooth transition between the high strength proximal portion 254 and the relatively short distal section 256 and retains a torque transmitting relationship between these two portions 254 and 256.

A helical coil 268 is disposed about the distal portion 256 and has a rounded plug 270 on the distal end 272 thereof. The coil 268 is secured to the distal portion 256 at a proximal location 274 and at an intermediate location 276 by a suitable solder. A shaping ribbon 278 is secured by its proximal end 280 to the distal portion 256 at the same location 276 by the solder and by the distal end thereof 282 to the rounded plug 270 that is usually formed by soldering or welding the distal end of the coil 268 to the distal tip of the shaping ribbon 278. Preferably, the most distal section 284 of the helical coil 268 is made of radiopaque metal such as platinum, platinum-nickel, or iridium-tantalum alloys to facilitate the observation thereof by fluoroscopy while it is disposed within a patient's body. The most distal section 284 should be stretched about 10 to about 30 percent.

The most distal part 286 of the distal portion 256 is flattened into a rectangular section and preferably provided with a rounded tip 288, e.g., solder to prevent the passage of the most distal part 286 through the spacing between the stretched distal section 284 of the helical coil 268.

The exposed portion of the elongated proximal portion 254 should be provided with a coating 290 of lubricious material such as polytetrafluoroethylene (sold under the trademark Teflon® by du Pont, de Nemours & Co.) or other suitable lubricious coatings such as the polysiloxane coatings.

The elongated proximal portion 254 of the guide wire 250 is generally about 130 to about 140 cm in length with an outer diameter of about 0.15 to 0.46 mm (0.006 to 0.018 in.) for coronary use. Larger diameter guide wires may be employed in peripheral arteries and other body lumina. The lengths of the smaller diameter and tapered sections can range from about 2.0 to about 20 cm, depending upon the stiffness of flexibility desired in the final product. The helical coil 268 is about 20 to about 45 cm in length, has an outer diameter about the same size as the diameter of the elongated proximal portion 254, and is made from stainless steel wire about 0.005 to 0.008 mm (0.002 to 0.003 in.) in diameter. The shaping ribbon 278 and the flattened distal section 288 of the distal portion 256 have rectangular transverse cross-sections that usually have dimensions of about 0.023 by 0.076 mm (0.001 by 0.003 in.).

The hypotubing from which the connector 258 is formed generally may have an outer diameter from about 0.15 to about 0.51 mm (0.006 in. to about 0.02 in.) with wall thicknesses of about 0.025 to about 0.102 mm (0.001 to about 0.004 in.). A presently preferred superelastic hypotubing for the connecting member 258 has an outer diameter of about 0.356 mm (0.014 in.) and a wall thickness of about 0.051 mm (0.002 in.).

The superelastic members of the invention, i.e., the distal portion 256 and the connector 258, are preferably made of an alloy material composition including, by atomic percent, about 28 to about 52 percent nickel, preferably from about 34 to about 49 percent nickel; from about 48 to about 52 percent titanium; and up to about 20 percent of at least one alloying element selected from the group consisting of palladium, chromium, and hafnium. When the alloying element is palladium or hafnium, the alloying element is preferably present in a range from about 3 to about 20 percent, more preferably, from about 5 to about 11 percent. When the alloying element is chromium, the alloying element is preferably present up to about 3 percent, more preferably, from about 0.1 to about 1 percent, and most preferably from about 0.2 to about 0.5 percent. Preferably, the alloying element is palladium. Of course, the alloy material composition may include further elements of improving other desirable features such as manufacturability. The alloy material of the present invention has an increased ultimate tensile strength and tensile yield strength. This increase in the ultimate tensile strength and tensile yield strength provides for a guide wire having at least substantially the superelasticity and kink resistance of a guide wire made of NITINOL and substantially the increased modulus of elasticity and tensile strength of a guide wire made of stainless steel.

A presently preferred method for making the final configuration of the superelastic portions of the guiding member is to cold work, preferably by drawing, a rod or tubular member having a composition according to the relative proportions described above and then heat treating the cold worked product while it is under stress to impart a shape memory thereto. Typical initial transverse dimensions of the rod or the tubular member are about 0.045 inch and about 0.25 inch respectively. If the final product is to be tubular, a small diameter ingot, e.g., 0.25 to about 1.5 inch in diameter and 5 to about 30 inches in length, may be formed into a hollow tube by extruding or by machining a longitudinal center hole therethrough and grinding the outer surface thereof smooth. Before drawing the solid rod or tubular member, it is preferably annealed at a temperature of about 500 degrees to about 750 degrees C, typically about 650 degrees C, for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stressed relieved stock is cold worked by drawing to effect a reduction in the cross sectional area thereof at about 30 to about 70 percent. The metal is drawn through one or more dies of appropriate inner diameter with a reduction per pass of about 10 to 50 percent. Other forms of cold working can be employed such as swaging.

Following cold work, the drawn wire or hollow tubular product is heat treated at a temperature between about 350 degrees and about 600 degrees C for about 0.5 to about 60 minutes. Preferably, the drawn wire or hollow tubular product is simultaneously subjected to a longitudinal stress between about 5 percent and about 50 percent, preferably about 10 percent to about 30 percent of the tensile strength of the material (as measured at room temperature) in order to impart a straight "memory" to the metal and to ensure that any residual stresses therein are uniform. This memory imparting heat treatment also fixes the austenite-martensite transformation temperature from the cold worked metal. By developing a straight "memory" and maintaining uniform residual stresses in the superelastic material, there is little or no tendency for a guide wire made of this material to whip when it is torqued within a patient's blood vessel.

An alternate method for imparting a straight memory to the cold worked material includes mechanically straightening the wire or tube and then subjecting the straightened wire to a memory imparting heat treatment at a temperature of about 300 degrees to about 450 degrees C, preferably about 330 degrees C to about 400 degrees C. The latter treatment provides substantially improved tensile properties, but it is not very effective on materials that have been cold worked above 55 percent, particularly above 60 percent. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

The high strength proximal portion 254 of the guide wire generally is stronger, i.e., higher ultimate tensile strength, than the superelastic distal portion 256. Suitable high strength materials include 304 stainless steel which is a conventional material in guide wire construction.

Alternatively, due to the higher ultimate tensile strength and higher yield point of the alloy material of the present invention, other portions of the guide wire previously formed from stainless steel may also be formed from the alloy material of the present invention. For example, in another embodiment, in addition to the distal portion of the core, one or more of the proximal portions 254, the connector 258, and the flattened most distal part 286 of the distal portion 256 may be formed from the alloy material of the present invention.

In another embodiment, the entire guide wire core 252 may be formed of the alloy material of the present invention. In addition, when the entire guide wire core 252 is formed of the present alloy material, the proximal portion 252 and the distal portion 256 are integral with one another without the presence of the connector 258. A guide wire of this configuration would appear more like that shown in FIG. 1. Further, a guide wire in accordance with FIGS. 7, 8, and 9 may have threads at its proximal end, as shown in FIG. 1, or may be used with the crimp screw 50 shown in FIGS. 2 and 3.

The present invention provides guide wires that have superelastic characteristics to facilitate the advancing thereof in a body lumen. The guiding members exhibit extensive, recoverable strain resulting from stress induced phase transformation of austenite to martensite at exceptionally high stress levels that greatly minimizes the risk of damage to arteries during the advancement therein.

As will be apparent to those skilled in the art, the ultrasound transmission guide wire shown and described herein is particularly suited to treating smaller, more distal vessels with ultrasonic energy. The ultrasound guide wire shown and described herein is suited for use with arterial lesions also. At the same time, the same guide wire is capable of functioning with a conventional ultrasound catheter system that can be used conveniently to provide balloon angioplasty and/or stent delivery to a patient. The same guide wire can also be used in ways similar to many other conventional guide wires for other procedures. The small size of the ultrasound transmission guide wire disclosed herein enables it to be used to cross, and provide ultrasonic therapy to, chronic total occlusions.

Although the invention has been described herein with specific reference to presently preferred embodiments thereof, it will be appreciated by those skilled in the art that various additions, modifications, deletions and alterations may be made to such preferred embodiments thereof without departing from the spirit and scope of the invention. Accordingly, it is intended that the invention not be limited, except as by the appended claims.

What is claimed is:

1. An ultrasound transmission guide wire for use in an ultrasonic angioplasty device, the ultrasound transmission guide wire having an elongated shaft, a proximal end configured to be connected to an ultrasound transducer, and a distal end for applying ultrasonic energy to an area of vascular lesion, the ultrasound transmission guide wire comprising:

a distal portion with at least one amplification region of reduced cross-sectional diameter, wherein the location and dimensions of each amplification region are selected so as to reduce the possibility of breakage of the ultrasound transmission guide wire due to transverse vibrations of ultrasonic energy;

a core of ultrasonic transmission material; and a non-metallic outer jacket in contact with and surrounding the core along each amplification region, the outer jacket having a substantially constant thickness, wherein the outer jacket further reduces the possibility of breakage of the ultrasound transmission guide wire due to transverse vibrations of ultrasonic energy.

2. The ultrasound transmission guide wire of claim 1 wherein the ultrasound transmission guide wire comprises threads disposed at its proximal end, the threads configured to connect to a connecting device for an ultrasound transducer to thereby communicate ultrasonic energy to the elongated shaft and to the distal end of the ultrasound transmission guide wire.

3. The ultrasound transmission guide wire of claim 1 wherein the ultrasound transmission guide wire comprises a first generally cylindrical section having a first cross-sectional diameter, and a second generally cylindrical section distal to the first section and having a second cross-sectional diameter that is smaller than the first cross-sectional diameter, the amplification region being formed at a proximal portion of the second generally cylindrical section.

4. The ultrasound transmission guide wire of claim 3 further comprising a conically tapered section interposed between the first and second cylindrical sections.

5. The ultrasound transmission guide wire of claim 4 further comprising a plurality of conically tapered sections interposed between adjacent ones of the plurality of generally cylindrical sections.

6. The ultrasound transmission guide wire of claim 1 further comprising a plurality of generally cylindrical sections, each of the plurality of generally cylindrical sections having reduced cross-sectional diameter relative to a proximal adjacent section resulting in a plurality of amplification regions in the cylindrical sections of reduced cross-sectional diameter.

7. The ultrasound transmission guide wire of claim 1 further comprising an enlarged application portion located at the distal end of the elongated shaft, the enlarged application portion configured to apply ultrasonic energy to a biological lesion.

8. The ultrasound transmission guide wire of claim 7 wherein the enlarged application portion comprises a rounded portion having a diameter exceeding the diameter of the elongated shaft immediately proximal to the rounded portion.

9. The ultrasound transmission guide wire of claim 8 wherein the enlarged application portion comprises a smooth ball tip having a diameter exceeding the diameter of the elongated shaft immediately proximal to the ball tip.

10. The ultrasound transmission guide wire of claim 1 wherein the outer jacket is formed of shrink tubing.

11. The ultrasound transmission guide wire of claim 1 wherein the outer jacket is formed of rubber.

12. The ultrasound transmission guide wire of claim 1 wherein the outer jacket is formed of plastic.

13. The ultrasonic angioplasty catheter device of claim 1 wherein the ultrasound transmission guide wire is formed at least partially of a superelastic metal alloy.

14. The ultrasonic angioplasty catheter device of claim 1 wherein the ultrasound transmission guide wire is formed at least partially of a shape memory alloy that exhibits superelastic properties when in its martensitic state.

15. The ultrasonic angioplasty catheter device of claim 14 wherein the ultrasound transmission guide wire is formed of a nickel-titanium alloy.

16. An ultrasound transmission guide wire having an elongated shaft, a proximal end configured to be connected to an ultrasound transducer, and a distal end for applying ultrasonic energy, the ultrasound transmission guide wire comprising:
a distal portion with at least one amplification region of reduced cross-sectional diameter, wherein the location and dimensions of each amplification region are selected so as to reduce the possibility of breakage of the ultrasound transmission guide wire due to transverse vibrations of ultrasonic energy;
a core of ultrasonic transmission material;
an enlarged application portion located at the distal end of the elongated shaft, the enlarged application portion configured to apply ultrasonic energy; and
a non-metallic outer jacket in contact with and surrounding the core along each amplification region, wherein the outer jacket further reduces the possibility of breakage of the ultrasound transmission guide wire due to transverse vibrations of ultrasonic energy.

17. The ultrasound transmission guide wire of claim 16 further comprising a plurality of generally cylindrical sections, each of the plurality of generally cylindrical sections having reduced cross-sectional diameter relative to a proximal adjacent section resulting in a plurality of amplification regions in the cylindrical sections of reduced cross-sectional diameter.

18. The ultrasound transmission guide wire of claim 17 further comprising a conically tapered section interposed between a pair of cylindrical sections.

19. The ultrasound transmission guide wire of claim 17 further comprising a plurality of conically tapered sections interposed between adjacent ones of the plurality of generally cylindrical sections.

20. The ultrasound transmission guide wire of claim 16 wherein the enlarged application portion comprises a smooth ball tip having a diameter exceeding the diameter of the elongated shaft immediately proximal to the ball tip.

21. The ultrasound transmission guide wire of claim 16 wherein the ultrasound transmission guide wire comprises threads disposed at its proximal end, the threads configured to connect to a connecting device for an ultrasound transducer to thereby communicate ultrasonic energy to the elongated shaft and to the distal end of the ultrasound transmission guide wire.

22. The ultrasonic angioplasty catheter device of claim 16 wherein the ultrasound transmission guide wire is formed at least partially of a superelastic metal alloy.

23. The ultrasonic angioplasty catheter device of claim 16 wherein the ultrasound transmission guide wire is formed at least partially of a shape memory alloy that exhibits superelastic properties when in its martensitic state.

24. The ultrasonic angioplasty catheter device of claim 23 wherein the ultrasound transmission guide wire is formed of a nickel-titanium alloy.

25. An ultrasonic angioplasty catheter device comprising an elongate flexible catheter having a proximal end, a distal end, and at least one lumen extending longitudinally therethrough, the device comprising:
an ultrasound transmission guide wire extending through the lumen and having a distal end with an enlarged head for applying ultrasonic energy to a lesion, and a proximal end configured to be connected to an ultrasound generating device, the ultrasound transmission guide wire having a distal portion with at least one amplification region of reduced cross-sectional diameter where transverse vibration of ultrasonic energy transmitted by the ultrasound transmission guide wire is amplified, wherein the location and dimensions of each amplification region are selected so as to reduce the possibility of breakage of the ultrasound transmission guide wire due to the transverse vibration;
wherein the ultrasound transmission guide wire comprises:
an elongated shaft;
a core of ultrasonic transmission material; and
an outer jacket surrounding the core along each amplification region.

26. The ultrasonic angioplasty catheter device of claim 25 wherein the ultrasound transmission guide wire is formed at least partially of a superelastic metal alloy.

27. The ultrasonic angioplasty catheter device of claim 25 wherein the ultrasound transmission guide wire is formed at least partially of a shape memory alloy that exhibits superelastic properties when in its martensitic state.

28. The ultrasonic angioplasty catheter device of claim 27 wherein the ultrasound transmission guide wire is formed of a nickel-titanium alloy.

* * * * *